(12) United States Patent
Augustine

(10) Patent No.: US 11,602,410 B1
(45) Date of Patent: *Mar. 14, 2023

(54) AERODYNAMIC SURGICAL LIGHT AND BOOM SYSTEMS

(71) Applicant: Augustine Biomedical + Design, LLC, Eden Prairie, MN (US)

(72) Inventor: Scott D. Augustine, Deephaven, MN (US)

(73) Assignee: Augustine Biomedical + Design, LLC, Eden Prairie, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/987,125

(22) Filed: Nov. 15, 2022

Related U.S. Application Data

(63) Continuation of application No. 17/719,840, filed on Apr. 13, 2022, now Pat. No. 11,529,209.

(60) Provisional application No. 63/175,907, filed on Apr. 16, 2021.

(51) Int. Cl.
| | |
|---|---|
| *A61B 90/30* | (2016.01) |
| *F21V 21/40* | (2006.01) |
| *F21V 21/28* | (2006.01) |
| *F21Y 115/10* | (2016.01) |
| *F21W 131/205* | (2006.01) |

(52) U.S. Cl.
CPC .............. *A61B 90/30* (2016.02); *F21V 21/28* (2013.01); *F21V 21/403* (2013.01); *A61B 2090/306* (2016.02); *F21W 2131/205* (2013.01); *F21Y 2115/10* (2016.08)

(58) Field of Classification Search
CPC ... A61B 90/30; A61B 2090/309; F21V 21/21; F21V 21/28; F21V 21/403; F21W 2131/205; F21Y 2115/10

USPC ............................................ 600/249; 362/33
See application file for complete search history.

(56) References Cited

U.S. PATENT DOCUMENTS

| | | | |
|---|---|---|---|
| 7,851,741 | B2 | 12/2010 | Tseng |
| 8,066,802 | B2 | 11/2011 | Kristensson et al. |
| 8,424,833 | B2 | 4/2013 | Mueller et al. |

(Continued)

OTHER PUBLICATIONS

"U.S. Appl. No. 17/719,840, Ex Parte Quayle Action dated Jul. 21, 2022", 9 pgs.

(Continued)

*Primary Examiner* — Lau K Tso
(74) *Attorney, Agent, or Firm* — Schwegman, Lundberg & Woessner, P.A.

(57) ABSTRACT

Disclosure herein are aerodynamic surgical lights and methods of manufacturing and use thereof. The aerodynamic surgical lights may include a light head made of one or more substantially tubular light housings. The substantially tubular light housings contain and protect a plurality of LED lights and their respective reflectors that aim a light beam toward the lower side of the substantially tubular light housings. The substantially tubular light housings are vertically elongate. The vertically elongated substantially tubular light housings include upper sections that are aerodynamically curved or pointed to streamline airflow past the light housings. The upper sections of the substantially tubular light housings are made of molded plastic resin reinforced with carbon fibers or glass fibers and the lower sections of the substantially tubular light housings are made of a clear moldable plastic.

30 Claims, 8 Drawing Sheets

(56) References Cited

U.S. PATENT DOCUMENTS

| | | |
|---|---|---|
| 2006/0082997 A1 | 4/2006 | Derrien et al. |
| 2011/0079697 A1 | 4/2011 | Mueller et al. |
| 2012/0043915 A1 | 2/2012 | Rohwedder et al. |
| 2016/0091170 A1* | 3/2016 | Watanabe ............. F21V 7/0008 362/237 |
| 2022/0331046 A1 | 10/2022 | Augustine |

OTHER PUBLICATIONS

"U.S. Appl. No. 17/719,840, Notice of Allowance dated Oct. 3, 2022", 8 pgs.

"U.S. Appl. No. 17/719,840, Response filed Sep. 21, 2022 to Ex Parte Quayle Action dated Jul. 21, 2022", 14 pgs.

\* cited by examiner

AERODYNAMIC SURGICAL LIGHT AND BOOM SYSTEMS

PRIORITY

This application is a continuation of U.S. patent application Ser. No. 17/719,840, filed Apr. 13, 2022, which claims the benefit of priority to U.S. Provisional Application Ser. No. 63/175,907, filed Apr. 16, 2021, which is incorporated by reference herein in its entirety.

TECHNICAL FIELD

This document pertains generally, but not by way of limitation, to surgical lights.

BACKGROUND

Surgical lights are used in operating rooms to provide light to illuminate a patient and surgical tools in an operating room. Surgical lights can be located on a boom or a stand for positioning over the patient during a procedure.

SUMMARY

In addition to being directed to surgical lights, the present disclosure includes systems and methods for improving safety in operating rooms (OR). In particular, the systems and methods described herein may include but are not limited to, minimizing the airflow obstructions that may disrupt the OR ventilation airflow that is meant to protect the sterile surgical field.

The sterility of the air of the surgical field in the modern operating room (OR) is meant to be protected and maintained by filtered air flowing downward from large vents in the ceiling above the surgical table. The theory is that the downward flowing air pushes any airborne particles and pathogens downward to the floor or out the exhaust vents located near the floor.

There are two generally accepted types of OR ventilation: conventional and laminar flow. Conventional OR ventilation consists of multiple air inlet vents mounted in the ceiling above the surgical table, each blowing a jet of air toward the surgical table. These jets of air are well-known to cause massive turbulence in the air of the sterile field. Turbulence both expels air and entrains air, making a clean sweep of airborne particles from the surgical field air, problematic. Laminar flow ventilation in contrast, flows from the ceiling through vents that cover the entire area above the surgical table—typically a square that is 8-9 feet on a side. Laminar flow is defined as air flowing in parallel layers with no disruption between those layers. In other words, there is no turbulence in laminar flow ventilation and the downward-moving river of highly filtered air can make a clean sweep of airborne particles from the air over the surgical field.

Laminar flow ventilation has been shown in some studies to be much more protective and in other studies to have no advantage over conventional ventilation. One possible explanation for these contradicting results is that laminar flow is very sensitive to disruption. We have recently shown in our laboratory that there are two primary causes of laminar flow disruption in the OR. First is the flow obstruction caused by the equipment such as surgical lights and equipment booms that are typically hanging from the ceiling inside the ventilation flow field. Surgical light "heads" are typically shaped like a horizontal disk that is 30-36 inches in diameter. Additionally, the trend in OR design of hanging much of the equipment from ceiling has introduced relatively massive steel booms that may be as large as 8 inches wide by 6 inches high, into the air above the sterile surgical field. The most obvious determinant of the degree of flow obstruction is the size of the surface area obstructing the airflow. A 36 inch diameter disk for example, is a very large area of obstruction considering that it may be located less than 36 inches from the top of the patient on the surgical table.

Next, in engineering terms this disc-shaped light head design would be described as a "flat plate perpendicular to the flow" which results in nearly the highest "drag coefficient" of any possible design. The higher the drag coefficient, the less aerodynamic the design. The relatively flat surface on the side of the light head facing the airflow (top side) induces significant turbulence as the downward ventilation airflow is forced to part in order to flow around the light head.

The inventors discovered that the relatively flat surface on the side of the light head facing away from the downward ventilation airflow (bottom side) is even more important in determining the adverse effect on the sterile field. For example, a 30-36 inch diameter light head prevents the air flowing around the edges of the light from smoothly recombining under the light head, resulting in a broad "wake" of turbulence and vortices that form under the light head. The broad "wake" of turbulence and vortices that form under the light head actually create a suction—a region of negative pressure relative to ambient, that can suck airborne particles into a vortex and keep them airborne for prolonged periods.

The relatively flat surfaces on both the side facing the air flow (top side) and the side facing away from the air flow (bottom side) of the light heads and booms are the exact opposite of "streamlined" aerodynamic design. The inventors discovered that the massive booms and lights hanging in the laminar flow field cause significant disruption of the laminar flow.

The second cause of laminar flow disruption in the OR is even less obvious—waste heat, especially the approximately 1000 watts of waste heat from a forced-air patient warming system (FAW). FAW systems work by blowing roughly 40 CFM of heated air into an air blanket positioned on the patient. The most common FAW blanket covers the chest and outstretched arms of the patient and the waste heat and air escapes from this blanket at the head end of the surgical table. The inventors discovered that the waste heat from an upper body FAW blanket preferentially forms into convection currents of warm air that rise along the anesthesia side of the vertical "anesthesia screen" drape at the head end of the surgical table. In this location, the rising warm air is "protected" from the downward ventilation air by the flow-boundary layer "dead zone" that forms next to the vertical anesthesia screen. However, the inventors discovered that even without the "protection" of the anesthesia screen "dead zone," a convection current of warm air forms and rises directly into the downward ventilation airflow. At this point, the rising warm air is along the anesthesia side of the anesthesia screen, outside the sterile surgical field.

Most ORs have 2-3 surgical lights. The largest light head is typically 30-36 inches in diameter and positioned above the head end of the surgical table, slightly overlapping the vertical anesthesia screen drape. In this location, approximately 25-33% of the light heads' lower surface is on the anesthesia side of the screen and ~67-75 of the light heads' lower surface is on the surgical side of the screen. The inventors discovered that the turbulence induced by ventilation air flowing past the disk-shaped light head creates a region of relative negative pressure (vacuum) within a large vortex that forms under the light head. The large vortex under the light head is much like a rotating horizontal cylinder, with its long axis oriented parallel to and adjacent the anesthesia screen. The direction of the rotation is downward on the side facing the surgical site and upward on the side facing the anesthesia screen. The rotation is energized by waste FAW heat passing through the anesthesia screen, warming the air on that side of the vortex and causing it to rise. The rotation is also energized by the downward ventilation airflow passing against the side of the vortex facing the surgical field, causing the vortex to rotate downward on that side.

The waste FAW heated air rising under or near the edge of the surgical light along the anesthesia screen gets sucked across the top edge of the anesthesia screen and into the relative vacuum that forms under the light head. The rising heat that is sucked horizontally into the top side of the vortex immediately under the light, further energizes the rotation of the vortex. The turbulent vortex not only prevents the ventilation airflow from clearing the air of the sterile surgical field, but it also entrains surgical smoke, airborne particles and pathogens, keeping these contaminates airborne in the sterile field rather than allowing them to be cleared by the laminar ventilation. Pathogens are a risk to the patient and the surgical smoke is a breathing risk to the surgical staff.

There is a need for surgical light heads and booms that minimize the obstruction to OR ventilation airflow by applying principles of aerodynamics to minimize turbulence, vortex formation and low-pressure region formation in the air of the sterile surgical field.

In some examples, the aerodynamic surgical light heads and booms of this disclosure minimize the size of the "blunt body" or "flat plate" surface area of both the side facing the OR ventilation airflow and the side facing away from the OR ventilation airflow.

In some examples, the light bulbs of this disclosure may be protectively located in one or more substantially tubular light housings that have an interior width that may be slightly larger than the diameter of an LED lights' reflector. Multiple light bulbs may be located along the length of the substantially tubular light housing. In some examples, the one or more substantially tubular light housings may be arranged in almost any pattern including but not limited to one or more circles or concentric circles, one or more squares, a "cross" shape or "H" shape in order to form a light head.

In some examples, the one or more substantially tubular light housings may be arranged in two concentric circles, the outer circle might have a diameter of 30-36 inches for example and the inner circle might have a diameter of 12-16 inches for example. This design allows relatively large open spaces or "thru-pass ducts" (in contrast to "bypass") between the concentric substantially tubular light housings, that allow relatively free airflow directly through the surgical light head. In some examples, between 33% and 90% of the total projected surface area of the surgical light head may be open space serving as thru-pass ducting. Air passing freely through the light head minimizes or even prevents the wake, turbulence and vacuum from forming on the lower side of the light.

In some examples, it may be aerodynamically advantageous for the substantially tubular light housings to be a vertically elongated shape in cross section. In some examples, the vertically elongated shape of the substantially tubular light housings in cross section, may include a substantially semi-circular lower section and a substantially parabolic upper section. Minimizing the width of the one or more substantially tubular light housings while vertically elongating the shape in cross section and choosing aerodynamically advantageous curves such as a substantially parabolic upper section, will minimize the wake, turbulence and vacuum forming on the lower side of the light housings.

In some examples, the walls of the upper section of the one or more substantially tubular light housings may be made of molded fiber-reinforced resin such as carbon fiber or fiberglass. The resulting structure is very light weight, very strong and rigid. If the upper walls of the substantially tubular light housings were made of carbon fiber or fiberglass, the resulting light head would not require any additional framing for strength. If the upper walls of the substantially tubular light housings were made of carbon fiber or fiberglass, it would be very easy to mold complex aerodynamic shapes. In some examples, the surgical light heads of this disclosure may weigh less than 20 lbs. In contrast, prior art light heads typically weigh ~100 lbs.

In some examples, the individual LED lights within the substantially tubular light housings are each mounted in their own cone-shaped reflector. In some examples, the walls of the lower section of the one or more substantially tubular light housings may be made of a clear plastic to cover the open lower side and protect the light bulbs inside while letting the lights shine downward. In some examples, the clear plastic lower section may be molded into a semi-circular shape in cross-section to avoid distortion of the light beams while maintaining an aerodynamically advantageous shape. The use of LED lights may be advantageous because they produce minimal heat and their color output can be adjusted.

In some examples, the substantially tubular light housings might be in the form of a circle that creates the outer perimeter of the surgical light head. Multiple light bulbs may be mounted at intervals around the entire circular length of the substantially tubular light housing.

In some examples, the surgical light of this disclosure eliminates the laterally attached boom arm(s) and pivot joints of the prior art lights by moving the distal boom arm joint to the geographical center of the light head. In some examples, a ball and socket type of joint may be located at the "geographical center" and "center of mass" of the light head which would be the center of a circular light head or the crossing point of a cross-shaped light head for example. In order for a surgical light head to be repositioned easily and stay in the position that it is put by the operator, the boom joint at the light head must be lined up directly with the center of mass or center of gravity of the light head. In some examples, the perfectly balanced center of gravity in all planes eliminates torque on the light head and allows a light head construction that does not require internal metal framing. In some examples, a short distal boom arm accesses the light head in the center of the upper side, eliminating the added weight, complexity and airflow obstructions of the side-mounted prior art surgical lights.

In some examples, these same aerodynamic principles may advantageously be applied to boom design as well. Even a massive steel boom arm that may be as large as 8 inches wide by 6 inches high could be replaced by one or more aerodynamically shaped boom arms. In some examples, the vertical dimension of an aerodynamic boom arm should be at least 2 times the horizontal dimension. The majority of the lifting strength is afforded by the vertical side walls of the square or rectangular tubing. Therefore, eliminating most of the steel in the width has little effect on the lifting strength of the boom arm. However, it significantly reduces the "blunt body" or "flat plate" surface area of both the side facing the OR ventilation airflow and the side facing away from the OR ventilation airflow. This change alone would greatly reduce the wake, turbulence and vacuum forming on the lower side of the boom arms.

In some examples, the cross-sectional shape of an aerodynamically shaped boom arm may have a substantially parabolic-shaped upper section and a substantially parabolic-shaped lower section. In some examples, the boom arms may be made of aluminum that has been extruded in the chosen aerodynamic shape and size.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document. Any combination of the features shown and described in this disclosure, including combinations of fewer or more features is within the content of this disclosure. Modules, systems and methods including individual features described herein, without combinations of features as shown in the examples (for the sake of brevity), are also within the scope of this disclosure.

DETAILED DESCRIPTION

The following detailed description is exemplary in nature and is not intended to limit the scope, applicability, or configuration of the invention in any way. Rather, the following description provides practical illustrations for implementing exemplary examples of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

As described herein, operably coupled can include, but is not limited to, any suitable coupling, such as a fluid (e.g., liquid, gas) coupling, an electrical coupling or a mechanical coupling that enables elements described herein to be coupled to each other and/or to operate together with one another (e.g., function together).

Directional indicators may be used with their normal customary meaning under typical orientation of function during surgery. For example, upper can reference a direction generally upward. For example, but not limited to, facing towards a ceiling during normal surgical use or the portion located above and facing away from a patient during normal surgical use. Likewise, lower can reference a direction generally below or facing away from a corresponding upper portion. For example, but not limited to, facing generally towards a floor or patient during normal surgical use or the portion facing towards the floor or patient during normal use. Example coordinates showing various directional indicators are provided throughout this disclosure, In some example, these directional indicators indicate directions, though in some instances, they can specifically describe an axis. For example, in prior art FIG. 1, directional indicators V, L1 and L2 describe a vertical or height directional indicator V, a lateral or width directional indicator L1, and a longitudinal or width directional indicator L2. Such a coordinate system can be used with various surgical light systems described herein.

Figure 1:
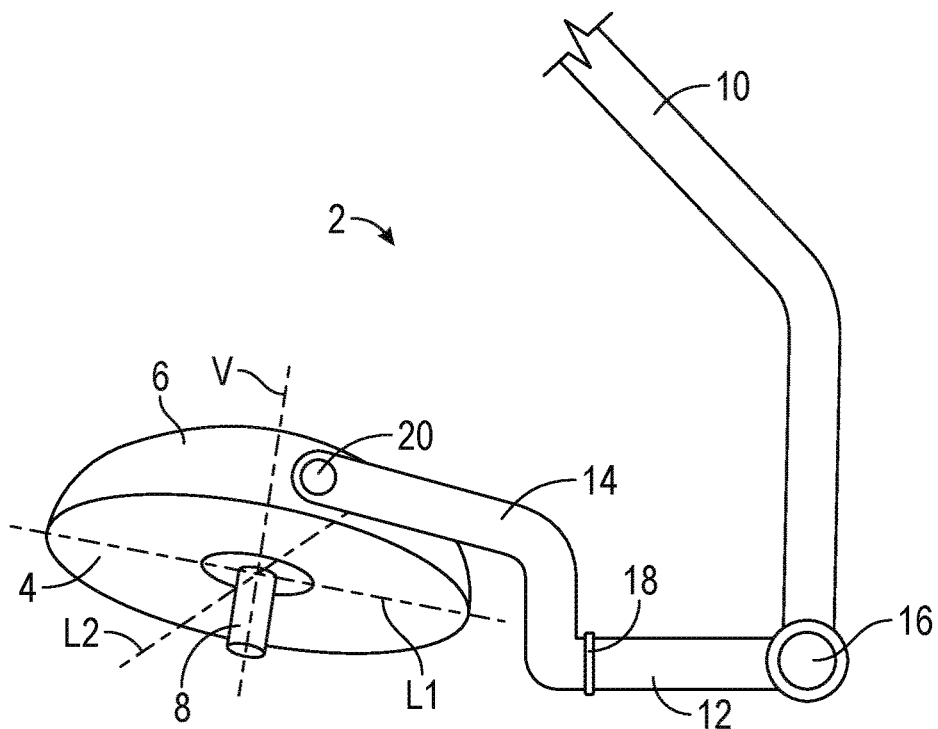
FIG. 1 shows a perspective view of an illustrative prior art surgical light, in accordance with at least one example.
Figure 2:
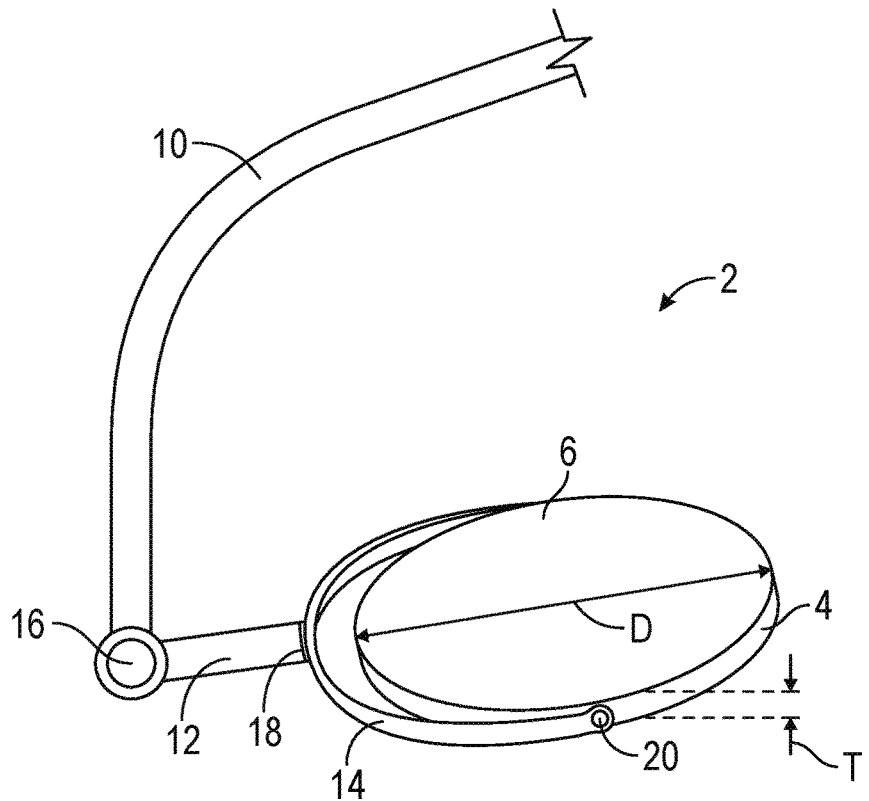
FIG. 2 shows a perspective view of an illustrative prior art surgical light, in accordance with at least one example.
Figure 3:
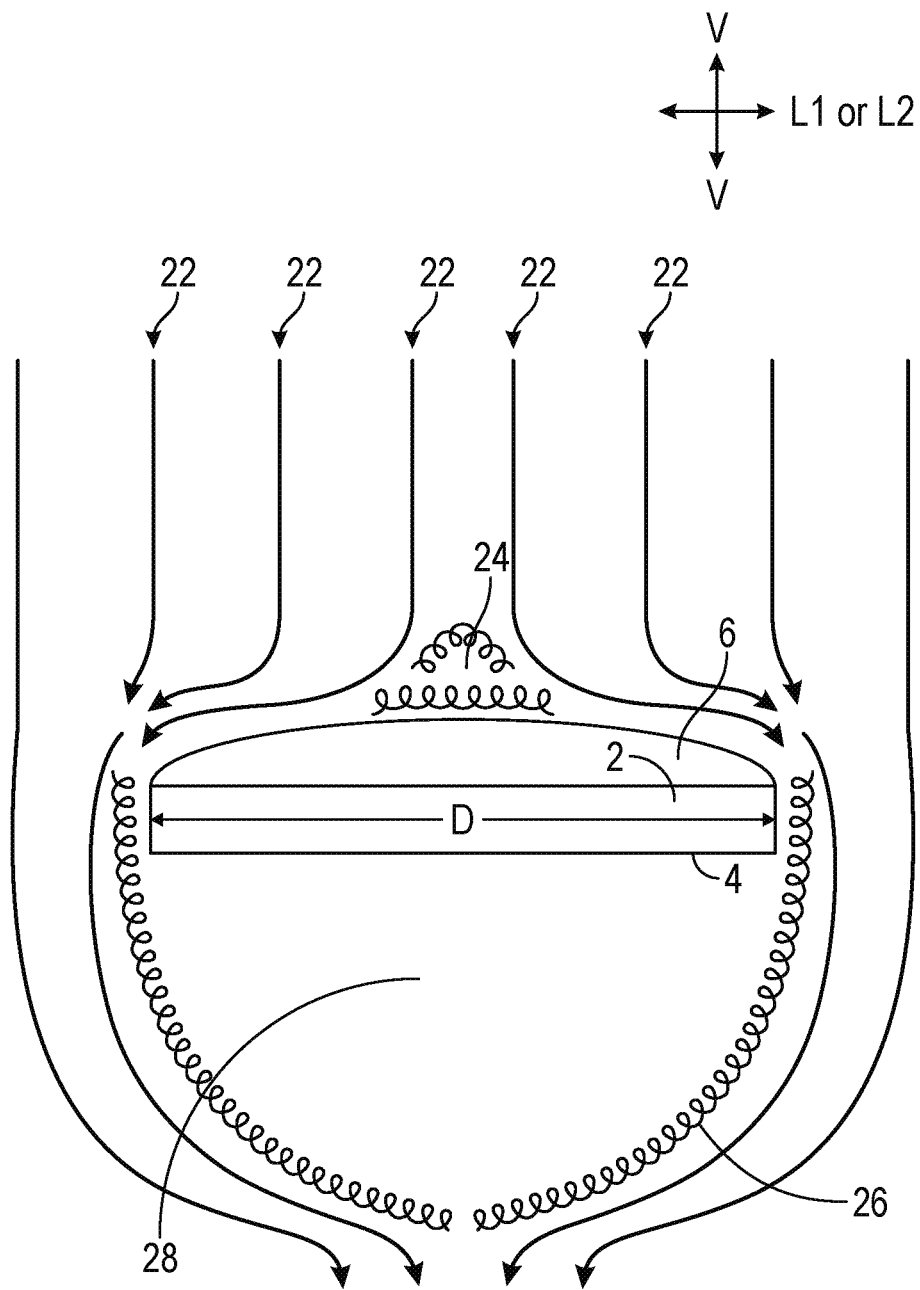
FIG. 3 shows a side view of an illustrative prior art surgical light and air currents flowing around it, in accordance with at least one example.

Examples of prior art surgical lights are shown in FIGS. 1,2 and 3, which are described together. Traditional surgical light head 2 designs house the light bulbs in large disc-shaped enclosures that may be 30-36 inches in diameter D and 4-12 inches thick T. Traditional surgical light heads 2 are substantially flat on their lower surface 4 and the upper surface 6 may be flat or slightly rounded. Prior art surgical lights have been made in many other shapes including squares, "H" shapes and multiple circles. All have a substantially flat lower surface 4 and a substantially flat or slightly rounded upper surface 6 in common.

Surgical lights are typically mounted to the ceiling of the OR through a series of boom arms and articulating joints. Extension arm 10 would typically be mounted to the pedestal (not shown) that is attached to the ceiling (not shown). Extension arm 10 typically attaches to articulating arm 12 through the extension/articulating joint 16. Articulating arm 12 typically attaches to yoke 14 through the arm/yoke joint 18. Yoke 14 typically attaches to the light head 2 through the yoke/light head joint 20. The yoke 14 may be single armed as shown in FIG. 1 or double armed as shown in FIG. 2. The various arms and joints of the boom system are designed to allow full movement of the light and to keep the light in the position that it is placed.

As shown in FIG. 3, in engineering terms this disc-shaped light head 2 design would be described as a "flat plate perpendicular to the flow" which results in nearly the highest "drag coefficient" of any possible design. The higher the drag coefficient, the less aerodynamic the design. The relatively flat upper surface 6 on the side of the light head 2 facing the laminar airflow 22 induces significant turbulence 24 as the downward ventilation airflow is forced to part in order to flow around the light head 2.

The relatively flat lower surface 4 on the side of the light head 2 facing away from the downward ventilation airflow (e.g., 22) is even more important in determining the adverse effect on the sterile field. A 30-36 inch diameter D light head prevents the air flowing around the edges of the light head 2 from smoothly recombining under the light head 2, resulting in a broad "wake" of turbulence and vortices 26 that form under the light head. The broad "wake" of turbulence and vortices 26 that form under the light head 2 actually create a suction—a region of negative pressure 28 relative to ambient, that can suck in airborne particles and keep them airborne for prolonged periods. This suction is similar to the suction that forms behind a semi-trailer on the highway. The air rushing past the flat back of the trailer produces tremendous vortices and a zone of negative pressure or partial vacuum immediately behind the trailer.

In some examples, the aerodynamic surgical light heads and booms of this disclosure minimize the size of the "blunt body" or "flat plate" surface area of both the side facing the OR ventilation airflow (e.g., upper surface 6) and the side facing away from the OR ventilation airflow (e.g., lower surface 4). In some examples as shown in a perspective view in FIG. 9, the surgical light head 92 of this disclosure minimizes the cross sectional area of the light housings 930A,B in order to minimize disturbances to the downward flowing OR ventilation. Open spaces or thru-pass ducts 940A-F in the light head 92 allow ventilation air to pass freely through the light head 92 in order to prevent the formation of a broad "wake" of turbulence, vortices and negative pressure from forming under the light head 92.

Figure 4:
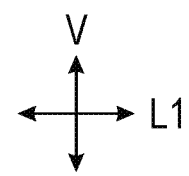
FIG. 4 shows a vertical cross-sectional view of an illustrative light housing, in accordance with at least one example.
Figure 4:
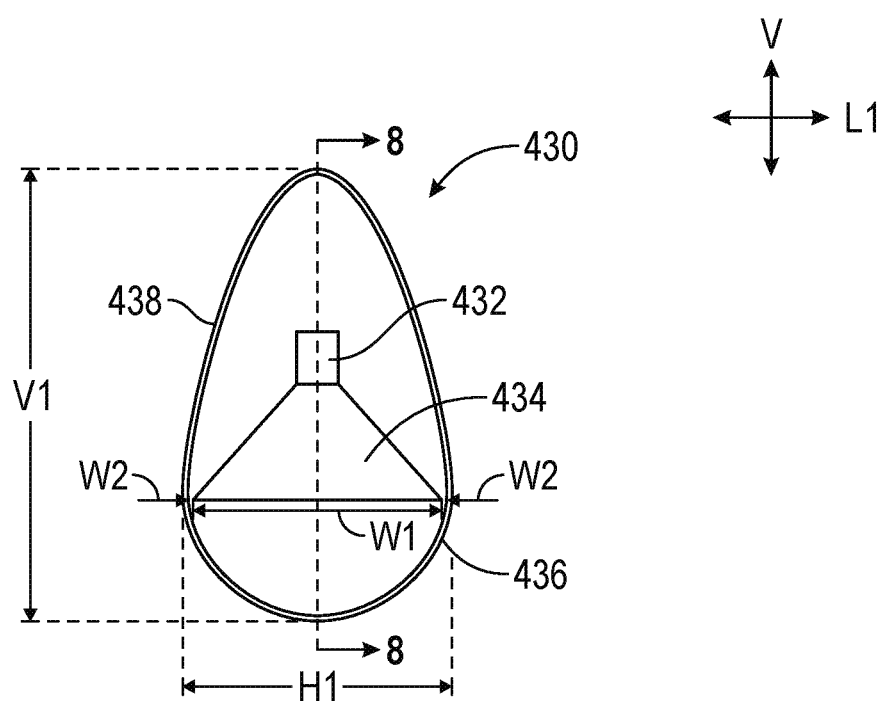

In some examples as shown in cross-section in FIG. 4, the light source such as LEDs or bulbs 432 of this disclosure may be protectively located in one or more substantially tubular light housings 430 that have an interior width that is slightly larger than the diameter of an LED lights' reflector 434. For example, if the diameter of the reflector 434 for a 2,000-3,000 lumen LED bulb 432 is 1.0 inch, the interior width W1 of the light housing 430 may be as little as 1.25 inches and the exterior width W2 of the light housing 430 may be as little as 1.5 inches. While minimizing the width of the light housings 430 may be advantageous, wider light housings 430 are also anticipated. In some examples the lower section 436 is made of a molded clear plastic that allows the light beam from LED 432 to shine out of the light housing 430. Suitable clear plastics include but are not limited to polycarbonate, acrylic and PVC.

Figure 5:
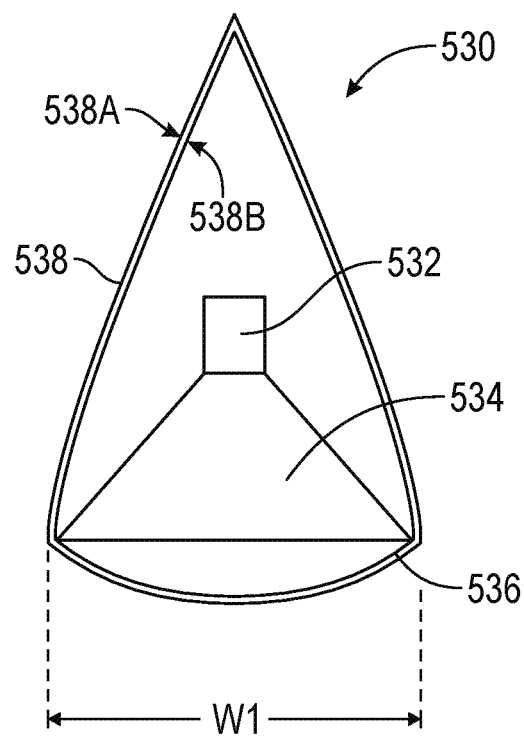
FIG. 5 shows a vertical cross-sectional view of an illustrative light housing, in accordance with at least one example.

In some examples, the one or more substantially tubular light housings 430 may be substantially circular in cross section. In some examples as shown in FIG. 4, the inventors have discovered that it may be aerodynamically advantageous for the substantially tubular light housings 430 to be a vertically elongated shape in cross-section such that the vertical dimension V1 is at least 1.5 times greater than the horizontal width H1. In some examples, the vertically elongated shape of the substantially tubular light housings 430 in cross section, may include a substantially semi-circular lower section 436 and a substantially parabolic upper section 438. In some examples as shown in FIG. 5, the vertically elongated shape of the substantially tubular light housings 530 in cross section, may include a curved lower section 536 and a substantially pointed upper section 538 much like a tear drop. Other combinations of elongate, streamlined aerodynamic shapes are anticipated. Minimizing the width, such as the maximum width W1, of the one or more substantially tubular light housings 430,530 while vertically elongating the shape in cross-section and choosing aerodynamically advantageous curves such as a substantially parabolic upper section 438, will minimize the wake, turbulence and vacuum forming on the lower side of the light housings 430,530.

Figure 6:
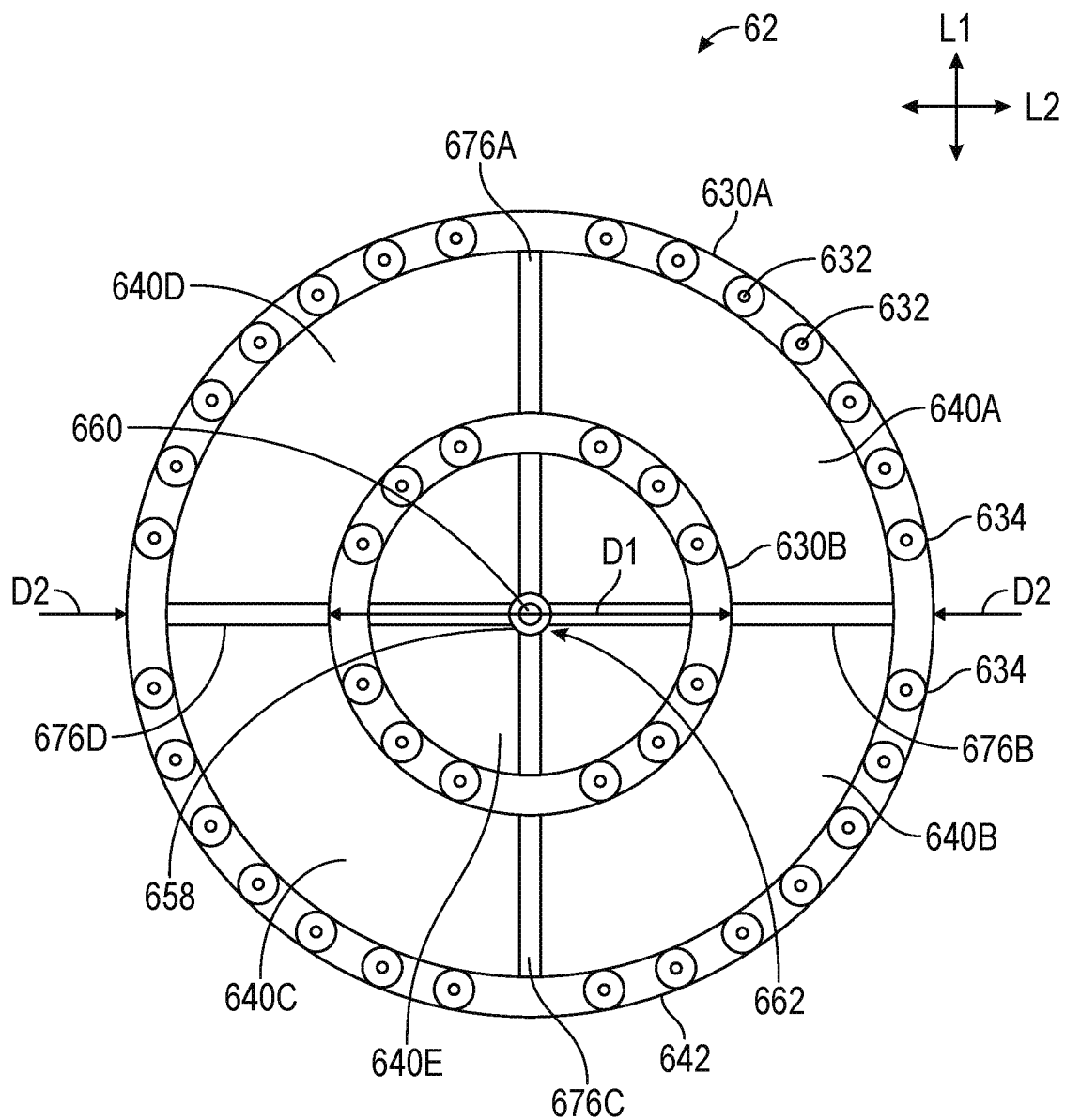
FIG. 6 shows a horizontal cross-sectional view of an illustrative light head, in accordance with at least one example.

As shown in horizontal cross-section in FIG. 6, multiple light bulbs 632 and reflectors 634 may be located along the length of the substantially tubular light housing 630A,B. In some examples, the one or more substantially tubular light housings 630A,B may be arranged in two concentric circles, the outer circle might have a diameter D1 of 30-36 inches for example and the inner circle might have a diameter D2 of 12-16 inches for example. This design allows relatively large open spaces or "thru-pass ducts" 640A-D between the concentric light housings 630A,B, that allow relatively free airflow directly through the surgical light head 62 (in contrast to "bypass ducts" that would direct the flow around the light head 62). In this example, if the light housings 630A,B were 1.5 inch in width, approximately 80% of the total projected surface area (e.g., within the outer perimeter 642) of the surgical light head 62 may be open space serving as thru-pass ducting 640A-D. In some examples, between 25% and 90% of the total projected surface area of the surgical light head 62 may be open space serving as thru-pass ducting 640A-D.

In the case of surgical lights, it is not feasible to simply make the total surface area of the light head smaller because the individual light bulbs must be spread out over a relatively large area in order to minimize shadow formation from the surgeon's head. Therefore, as shown in FIG. 6, in order to allow the lights to be spread out and yet minimize "blunt body" or "flat plate" surface area creating wake, turbulence and vacuums, large areas of open space or thru-pass ducts 640A-D are placed between the substantially tubular light housings 630A,B. Air passing freely through the light head 62 minimizes or even prevents the wake, turbulence and vacuum from forming on the lower side of the light head 62.

Figure 7:
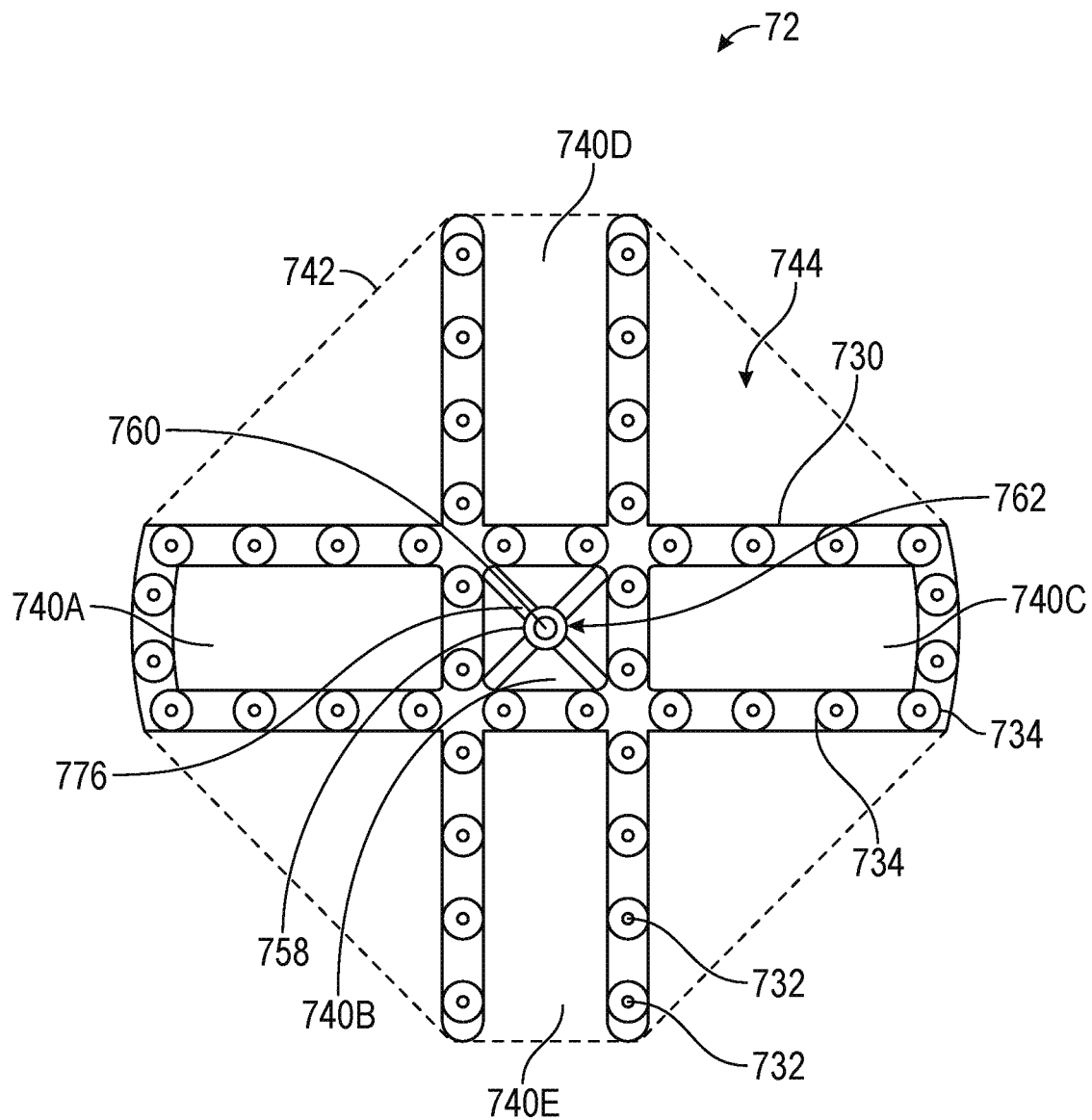
FIG. 7 shows a horizontal cross-sectional view of an illustrative light head, in accordance with at least one example.

In some examples, the one or more substantially tubular light housings 630A,B may be arranged in almost any pattern including but not limited to one or more: circles or concentric circles, squares, hexagons, "cross" shapes, "H" shapes or any other geometric shape in order to form a light head. For example as shown in FIG. 7, the light head 72 may be in a substantially "cross" shape. In this example, the thru-pass ducts 740A-C also include open spaces 740D,E. To calculate the percentage "surface" area represented by the thru-pass ducts, a perimeter 742 can be drawn around the tips of the light housings 730 and a total "surface" area 744 calculated. In the case of the circular light head 62 in FIG. 6, the perimeter 642 can be the outer dimension of the outer light housing 630A. The light head 72 can include lights 732, surrounded by reflectors 734

In some examples, the walls of the upper section 438,538 of the one or more substantially tubular light housings 430,530 may be made of molded fiber-reinforced resin such as carbon fiber or fiberglass. The resulting structure is very light weight, very strong and rigid. Polyester resin and other moldable resins are also anticipated. In some examples, the upper walls 438,538 of the substantially tubular light housings 430,530 are made of carbon fiber or fiberglass so that the resulting light head 62,72 does not require any additional framing for strength. Eliminating framing also eliminates some weight and complexity. In some examples, the upper walls 438,538 of the substantially tubular light housings 430,530 are made of carbon fiber or fiberglass so that complex aerodynamic shapes can be easily molded. In some examples, the upper walls 438,538 of the substantially tubular light housings 430,530 can be made of carbon fiber or fiberglass so that the outer surface of colored resin "gel coat" is more durable than paint and does not chip and fall into the sterile field if two lights bump into each other, as has been reported with painted steel lights and booms.

Other materials and constructions for the walls of the upper section 438,538 of the one or more substantially tubular light housings 430,530 are anticipated. For example, 3-D printing or "additive manufacturing" may be ideal for the complex design. Pressed metal such as aluminum can also be used. Combinations of materials may be advantageous. For example, an outer shell surface 538A may be 3-D printed and an inner layer 538B of fiber reinforced resin may be advantageously applied to provide added strength. Conversely, the outer shell 538 may be made of molded fiber reinforced resin and the interior partitions and fixtures may be 3-D printed.

In some examples, the walls of the lower section 436,536 of the one or more substantially tubular light housings 430,530 may be made of a clear plastic to cover the open lower side and protect the LED bulbs 432,532 inside, while allowing the lights shine downward. In some examples, the clear plastic lower section 436,536 may be molded into a semi-circular shape in cross-section as shown in FIGS. 4 and 5, to avoid distortion of the light beams while maintaining an aerodynamically advantageous shape. Substantially flat lenses (e.g., 436, 536) covering the reflector 434,534 are also anticipated.

Figure 8:
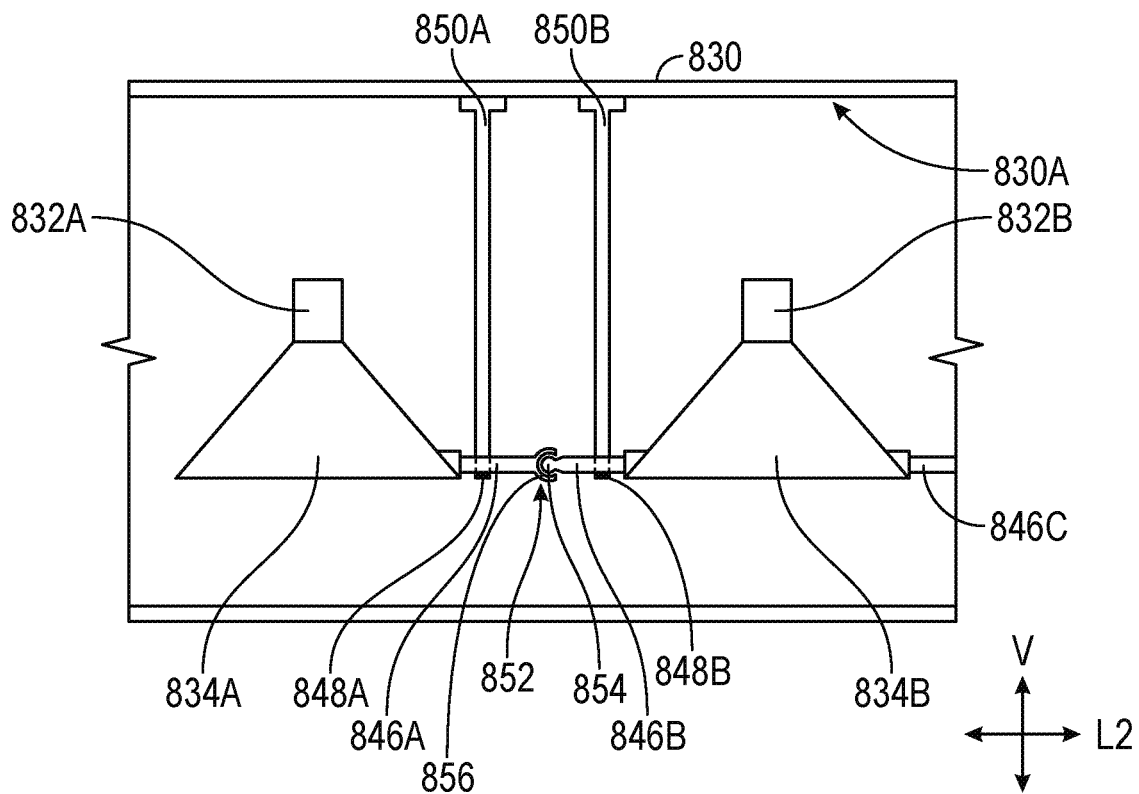
FIG. 8 shows a longitudinal cross-sectional view of an illustrative light housing, in accordance with at least one example. The cross-section view direction corresponds to a cross-section taken along the direction of line 8-8 in FIG. 4.

In some examples as shown in the vertical longitudinal section of FIG. 8 (e.g., a cross-sectional direction corresponding to a cross-section taken along line 8-8 in FIG. 4), the individual LED lights 832A,B within the substantially tubular light housing 830 may each be mounted in their own substantially cone-shaped reflector 834A,B. Reflectors with a generally parabolic shape and LED bulbs that do not require reflectors are also anticipated. In some examples, two small plastic or metal axils 846A-C are attached to opposite sides of the reflector 834A,B near to the open side of the reflector and project radially outward in the longitudinal axis of the substantially tubular light housing 830. The light axils 846A-C may be seated into bushings 848A,B on each side of the reflector 834A,B in the light housing 830 that orient the light axils 846A-C substantially parallel to the long axis of the substantially tubular light housing 830, allowing each light bulb 832A,B and its attached reflector 834A,B to pivot perpendicularly to the long axis of the substantially tubular light housing 830. Pivoting the lights 832A,B may be beneficial to refocus the multiple lights 832A,B as the depth of field changes due to the operators' repositioning the surgical light head 62,72 at different distances from the surgical site.

In some examples as shown in FIG. 6, the substantially tubular light housings 630A,B might be in the form of a circle that creates the outer perimeter 642 of the surgical light head 62. Multiple light bulbs 634 may be mounted proximate each other around substantially the entire circular length of the substantially tubular light housing 630A,B. In some examples, adjacent concentric circular substantially tubular light housings 630A,B may be connected together through spokes 676A-D in a "wheel and spoke" design. In some examples, spokes 676A-D may project inward to attach to the socket 658 at the geographic center of the light head 62. Spoke designs can be incorporated into other examples, such as the spokes 776 of FIG. 7.

In some examples as shown in FIG. 8, the light axils 846A,B are seated into bushings 848A,B on each side of the reflectors 834A,B and the bushings 848A,B may be mounted on cross members 850A,B. In some examples, cross members 850A,B are reinforcing partitions that are bonded to the inner wall 830A of the substantially tubular light housing 830 creating a honeycomb-like structure to provide mechanical strength and stiffness to the substantially tubular light housing 830. The cross members 850A,B may be made of plastic or metal and may be bonded to the walls of the light housing 830 with any suitable adhesive or resin.

In some examples, the adjacent axils 846A,B of adjacent lights 832A,B may be mechanically linked together through a flexible linkage 852. Linking adjacent lights 832A,B together allows the pivoting of one light 832A to cause an equal pivoting of the adjacent light 832B which causes the next light to pivot and so on around the whole circular length. Flexible linkages 852 include but are not limited to cables (not shown), ball-shaped Allen wrench heads 854 and sockets 856, "U joints" (not shown) or "lock and key" connectors (not shown) of various shapes.

Traditionally, surgical lights such as shown in FIG. 1, are focused by turning light handle 8. Turning light handle 8 pivots the individual lights inward or outward in order to keep the total light beam focused on the surgical site. As the light head 2 gets closer to the surgical field, the lights have to be directed more and more inward. The individual lights 432,532,632,732,832 of this disclosure can be easily rotated inward or outward in a coordinated fashion by linking a rotational movement of the light handle (e.g., 8; FIG. 1) to the linked chain of individual lights 432,532,632,732,832 through one or more linkages.

In order for a surgical light head to be repositioned easily and stay in the position that it is put by the operator, the boom joint at the light head must be lined up directly with the center of mass or center of gravity of the light head. As shown in FIGS. 1 and 2, the center of mass of prior art light heads 6 is inside the disk-shaped light head 2. In other words, the point at which the light head is balanced in any attitude (rotating up, down or sideways), is inside the volume of the light head 2 and therefore not accessible for a pivot joint. As a result, prior art disk-shaped light heads, are attached on their outside perimeter to the boom through either a single arm at 90° (as shown in FIG. 1) or a double armed "yoke" that is attached at both 90° and 270° (as shown in FIG. 2). If the disk-shaped light head is 6 inches thick for example, the center of mass will be approximately at the midpoint, about 3 inches from the light face. Pivoting at this location will prevent the light from naturally pitching forward or backward as its vertical angle is changed.

Further as shown in prior art FIGS. 1 and 2, side attachment pivot joints 20 to the light head 2 allow for a smooth vertical movement of the light head 2. However, this design requires a second pivot point, usually located at the arm/yoke joint 18 to allow side to side adjustments. As a result, these side attachment pivot joints result in several negative consequences. The distal boom arm or arms add weight, complexity and airflow obstructions. Attaching a single arm to one side of the light head creates a lever that applies considerable torque to the boom arm, the joint and the light head. This is especially important since the average prior art light head 2 weighs approximately 100 lbs., which is a lot of weight to support out at the end of multiple boom arms. One result is the need for an internal metal frame in the light head to handle the torque and support the weight. Metal frames take up space and add weight. In some examples, the light-weight light heads 62,72 of this disclosure do not require metal frames and weigh less than 20 lbs. Lighter weight light heads of this disclosure allows all of the support booms and arms to be lighter and also allows for easier repositioning of the surgical light by the operator.

In some examples as shown in FIGS. 6 and 7, the surgical light of this disclosure eliminates the laterally attached boom arm(s) and pivot joints of the prior art lights by moving the distal boom arm joint to the geographical center and center of mass of the light head 62,72. In some examples, a ball and socket type of joint 662,762 may be located at the geographical center of the light head 62,72 which would be the center of a circular light head 62 or the crossing point of a cross-shaped light head 72 for example. Since a ball and socket joint 662,762 can pivot both vertically and horizontally, one of the two single direction joints and boom arms of the prior art lights can be eliminated saving weight, complexity, cost and airflow disruption.

Figure 12:
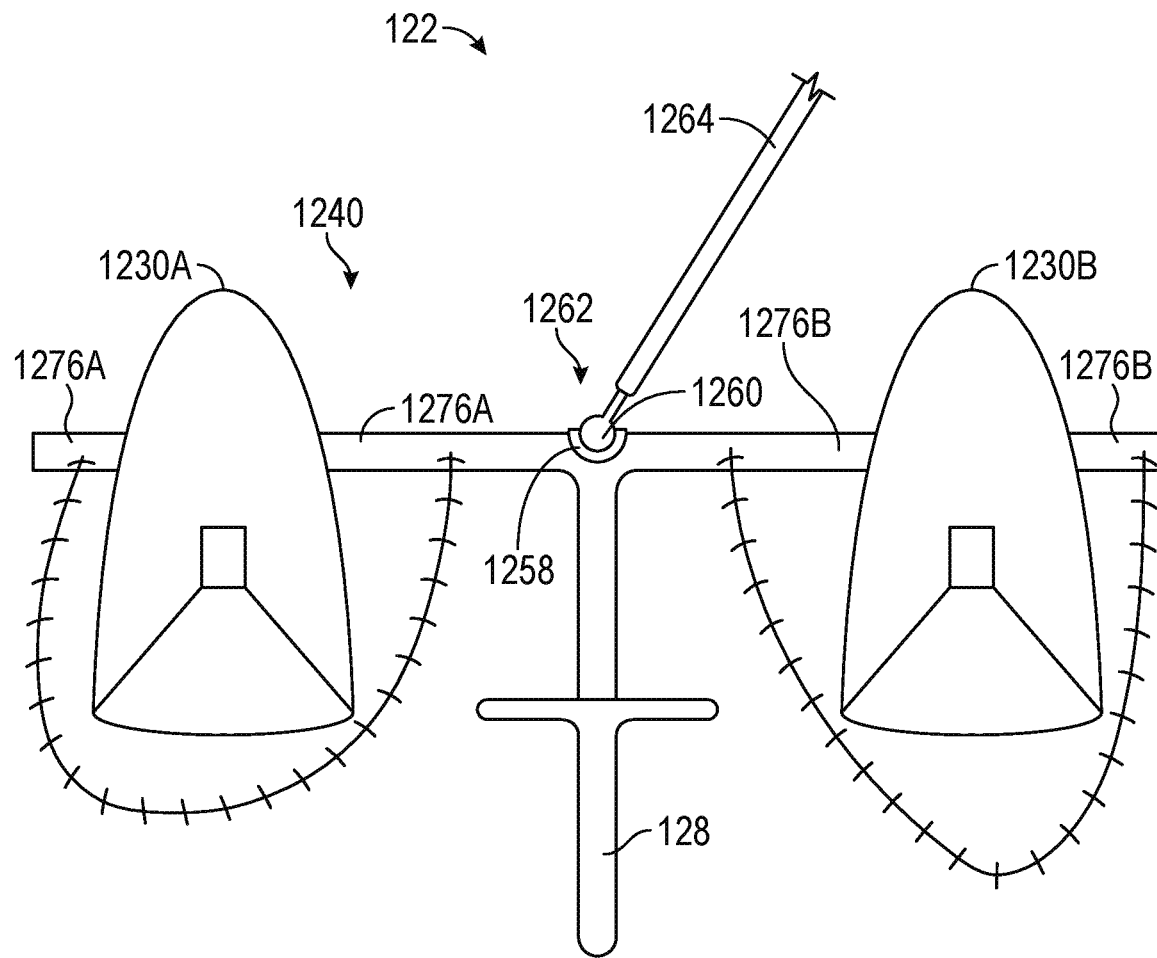
FIG. 12 shows cross-sectional view of an illustrative light system having a ball and socket type joint, in accordance with at least one example. The cross-section view corresponds to a cross-section taken along the direction of line 8-8 in FIG. 4.

In some examples as shown in FIGS. 6 and 7, a ball and socket type of joint 662,762 may be located at the geographical center of the light head 62,72. In some examples as shown in FIG. 12 a ball and socket type of joint 1262 may be located approximately midway between the uppermost and lowermost sides of the substantially tubular light housings 1230A,B in order to position the ball 1260 and socket 1258 of the joint 1262 at the exact center of mass (center of gravity) of the light head. In some examples, thru-pass ducts 640E,740B,1240 are located at the geographic center of the light head 62,72,122 in order to allow the ball and socket joint 662,762,1262 to be located within the volume of the light head 62,72,122 at the center of mass. In some examples, the substantially tubular light housings 630,730, 1230AB may be connected to the centrally located socket 1258 or ball 1260 of the joint 1262 by spokes 1276A,B.

Pivoting on a ball and socket joint located at the center of mass results in easy adjustment and the light head naturally stays in any position that it is put into by the operator, because it is in balance in all attitudes. Naturally staying in position advantageously eliminates the need for braking systems that add weight, complexity and resistance to movement. In some examples, positioning the ball and socket joint 662,762,1262 within the volume of the light head 62,72,122 at the center of mass, perfectly balances the center of gravity in all planes and eliminates torque on the light head, allowing a light head construction that does not require internal metal framing for strength.

Figure 9:
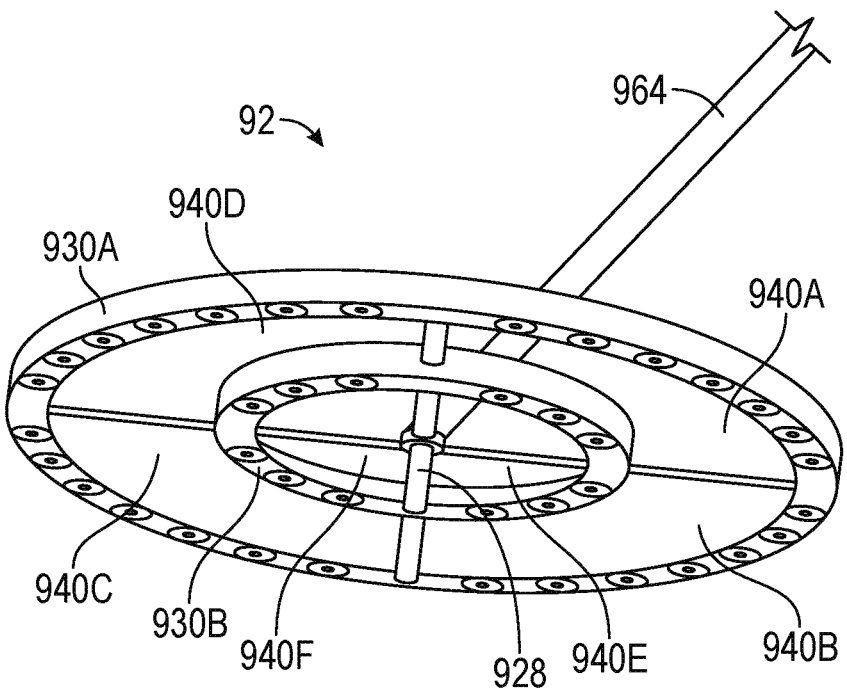
FIG. 9 shows a perspective view of an illustrative light head, in accordance with at least one example.

In some examples as shown in FIGS. 9 and 12, a short distal boom arm 964,1264 accesses the light head 92,122 in the center of the upper side, eliminating the added weight, complexity and airflow obstructions of the side-mounted prior art surgical lights (e.g., FIGS. 1-3). In some examples, the socket 658,758,1258 is structurally connected to the light head 62,72,122 and the ball 660,760,1260 is structurally connected to the distal arm 964,1264 of the boom system although the reverse is anticipated. In some examples, the short distal boom arm 964,1264 of this disclosure, eliminates the need for the prior art yoke 14, the arm/yoke joint 18 and the yoke/light head joint 20 shown in FIGS. 1 and 2. In some examples, as shown in FIGS. 9 and 12, the light handle 128,928 may be attached at the geographic center of the light head 92, 122.

In some examples, these same aerodynamic principles may advantageously be applied to boom design as well. Typically, prior art boom arms are made of square or rectangular steel tubing. The "extension arm" which is the most proximal boom arm attached to the ceiling pedestal mount, not only supports the most weight but also can experience massive torsional forces if the "articulating arm" is perpendicular to the extension arm. The prior art extension arm of some boom systems may be as large as 8 inches wide and 6 inches high. The articulating arms tend to be much smaller in cross section because they support less weight and do not experience the same torsional forces. Articulating arms may be 2 inches square or circular. Clearly the "blunt body" or "flat plate" surface area of an 8 inch-wide extension arm is significant and will produce a broad "wake" of turbulence and vortices under the boom arm.

Figure 10:
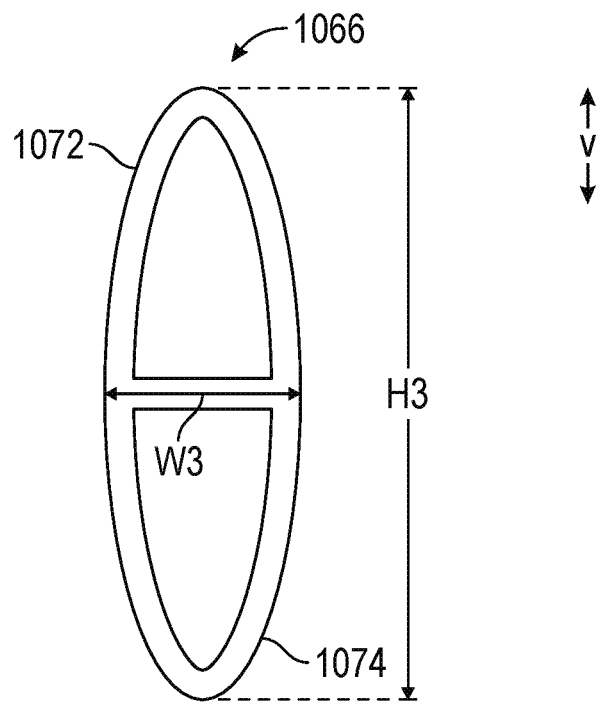
FIG. 10 shows a vertical cross-sectional view of an illustrative aerodynamic articulating boom arm, in accordance with at least one example.

In some examples as shown in cross-section in FIG. 10, an aerodynamically shaped boom arm for an articulating arm might be 1 inch wide and 3 inches high for example. In some examples, the vertical dimension of a boom arm should be at least 2 times the horizontal dimension. In this example, a 1 inch wide by 3 inch tall shape will be far more aerodynamic. Other dimensions are anticipated.

Replacing the prior art extension arms of some boom systems that may be as large as 8 inches wide and 6 inches high with aerodynamic arms is more challenging because extension arms must also tolerate torsional forces. In some examples as shown in cross-section in FIG. 11, an aerodynamically shaped extension boom arm 1168 might for example be made of two parallel 1.5 inch wide and 4 inches high articulating boom arms 1166A,B (other dimensions are anticipated). The two parallel articulating boom arms 1166A,B may be joined together with one or more reinforcing struts 1170, to form a beam structure with added torsional strength. The open spaces between the parallel booms 1166A,B and the reinforcing struts 1170 allow free airflow between the parallel booms 1166A,B. In some examples, the space between the two aerodynamically shaped parallel boom arms 1166A,B serves the same purpose as the thru-pass ducts 640,740 described above for the surgical lights.

In some examples as shown in FIG. 10, the cross-sectional shape of an aerodynamically shaped articulating boom arm 1066 may have a substantially parabolic-shaped upper section 1072 and a substantially parabolic-shaped lower section 1074. In some examples, the cross-sectional shape of an aerodynamically shaped boom arm may have a substantially pointed-shaped upper section and a substantially pointed-shaped lower section. In some examples, the cross-sectional shape of an aerodynamically shaped boom arm may have a substantially semicircular-shaped upper section and a substantially semicircular-shaped lower section. In some examples, the cross-sectional shape of an aerodynamically shaped boom arm may be any combination of these shapes or other suitable aerodynamic shapes.

Figure 11:
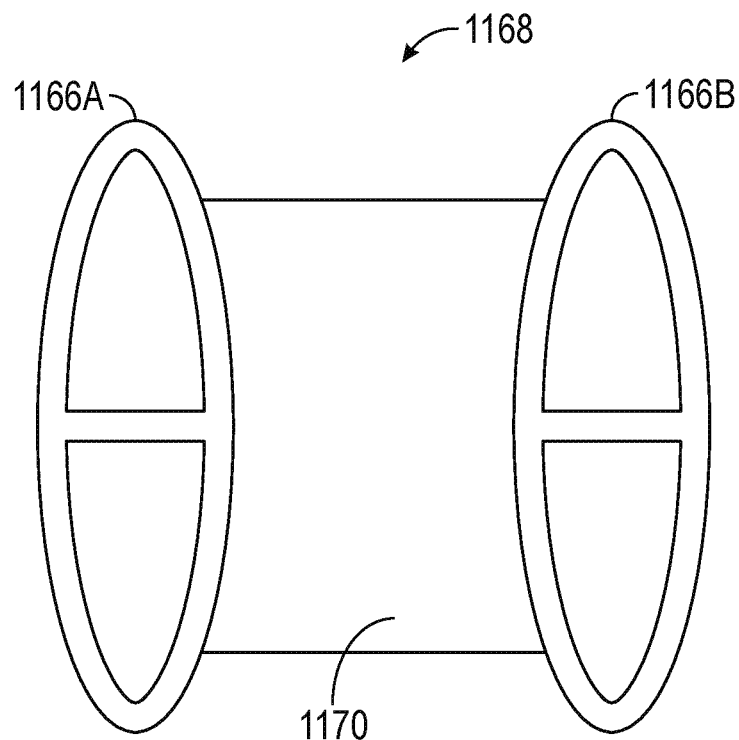
FIG. 11 shows a vertical cross-sectional view of an illustrative aerodynamic extension boom arm, in accordance with at least one example.

In some examples, the boom arms may be made of aluminum that has been extruded in the chosen aerodynamic shape and size. The superior strength of the boom arms 1066,1166 shown in FIGS. 10 and 11 is due to their cross-sectional shape, which means that they can be made of aluminum instead of prior art steel. In some examples, it may be desirable to make the boom arms 1066,1166 of this disclosure out of aluminum instead of the prior art steel, in order to make the entire boom system much lighter. Further, aluminum can be used to extrude complex shapes such as the boom cross section shown in FIG. 10.

Reducing the width W3 versus the height H3 of the boom arms of this disclosure compared to prior art boom arms and making their cross-sectional shape vertically elongate and adding aerodynamic curves to the upper and lower surfaces will significantly reduce the "blunt body" or "flat plate" surface area of both the side facing the OR ventilation airflow and the side facing away from the OR ventilation airflow. The boom arms of this disclosure would greatly reduce the wake, turbulence and vacuum forming on the lower side of the boom arms. The much lighter light head 92 of this disclosure allows lighter weight aluminum boom arms 1066,1166, both of which will drastically reduce the over-all weight of this boom system and lights compared to prior art surgical light boom systems. The reduced weight of the boom arm and surgical light system may allow installation onto operating room ceilings without requiring the massive superstructure currently needed to support prior art boom systems. This vastly reduces the complexity and cost of the boom and surgical light systems of this disclosure.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. The terms approximately, about or substantially can be defined as being within 10% of the stated value or arrangement.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

NOTES AND VARIOUS EXAMPLES

Example 1 is an aerodynamic surgical light, the aerodynamic surgical light comprising: a light head made of one or more substantially tubular light housings; and the substantially tubular light housings contain and protect a plurality of LED lights and their respective reflectors that aim a light beam toward the lower side of the substantially tubular light housings; and the substantially tubular light housings are vertically elongate with a vertical dimension at least 1.5 times greater than the horizontal width; and the vertically elongated substantially tubular light housings include upper sections that are aerodynamically curved or pointed to streamline airflow past the light housings; and the aerodynamic curves include but are not limited to: substantially parabolic shapes, substantially pointed shapes, substantially semicircular shapes and combinations thereof; and the upper sections of the substantially tubular light housings are made of molded plastic resin reinforced with carbon fibers or glass fibers; and the lower sections of the substantially tubular light housings are made of a clear moldable plastic; and the one or more substantially tubular light housings are connected together to form a geographic center of mass where the substantially tubular light housings connect to a ball and socket joint that connects the light housings to a supporting boom system.

In Example 2, the subject matter of Example 1 includes, wherein the one or more substantially tubular light housings are formed into one or more concentric substantially circular tubes with open spaces between the one or more concentric substantially circular tubes.

In Example 3, the subject matter of Example 2 includes, wherein the open spaces comprise greater than 40% of the projected surface area of the surgical light.

In Example 4, the subject matter of Examples 2-3 includes, wherein the one or more concentric substantially circular tubes with open spaces between the one or more concentric substantially circular tubes are connected together by spokes forming a "wheel and spoke" structure.

In Example 5, the subject matter of Example 4 includes, wherein the ball and socket joint and a light handle are connected to the center of the wheel and spoke structure.

In Example 6, the subject matter of Examples 1-5 includes, wherein the plurality of LED lights and their respective reflectors in the one or more concentric substantially circular tubes are each mounted on axils that allow the reflector and light to pivot from a first position shining straight downward collectively creating a cylinder of light to a second position shining inward collectively creating a cone of light.

In Example 7, the subject matter of Example 6 includes, wherein the adjacent axils of the adjacent lights are coupled to each other through flexible couplings allowing the positioning of one or more lights to dictate the position of all of the lights in each substantially circular tube.

In Example 8, the subject matter of Example 7 includes, wherein the flexible couplings include but are not limited to: cables, ball-shaped Allen wrench heads and sockets, "U joints" or "lock and key" connectors of various shapes.

In Example 9, the subject matter of Examples 1-8 includes, wherein the width of the substantially tubular light housings is less than three times the diameter of the LED reflectors.

Example 10 is an aerodynamic surgical light, the aerodynamic surgical light comprising: a light head made of one or more substantially tubular light housings; and the substantially tubular light housings contain and protect a plurality of LED lights and their respective reflectors that aim a light beam toward the lower side of the substantially tubular light housings; and the substantially tubular light housings are vertically elongate with a vertical dimension at least 1.5 times greater than the horizontal width; and the vertically elongated substantially tubular light housings include upper sections that are aerodynamically curved or pointed to streamline airflow past the light housings; and the aerodynamic curves include but are not limited to: substantially parabolic shapes, substantially pointed shapes, substantially semicircular shapes and combinations thereof; and the upper sections of the substantially tubular light housings are made of molded plastic resin reinforced with carbon fibers or glass fibers; and the lower sections of the substantially tubular light housings are made of a clear moldable plastic; and the one or more substantially tubular light housings are formed into one or more concentric substantially circular tubes with open spaces between the one or more concentric substantially circular tubes; and wherein the open spaces comprise greater than 40% of the projected surface area of the surgical light.

In Example 11, the subject matter of Example 10 includes, wherein the one or more concentric substantially circular tubes with open spaces between the one or more concentric substantially circular tubes are connected together by spokes forming a "wheel and spoke" structure.

In Example 12, the subject matter of Example 11 includes, wherein the one or more substantially tubular light housings are connected together to form a geographic center of mass where the substantially tubular light housings connect to a ball and socket joint that connects the light housings to a supporting boom system.

In Example 13, the subject matter of Example 12 includes, wherein the ball and socket joint and a light handle are connected to the center of the wheel and spoke structure.

In Example 14, the subject matter of Examples 10-13 includes, wherein the plurality of LED lights and their respective reflectors in the one or more concentric substantially circular tubes are each mounted on axils that allow the reflector and light to pivot from a first position shining straight downward collectively creating a cylinder of light to a second position shining inward collectively creating a cone of light.

In Example 15, the subject matter of Example 14 includes, wherein the adjacent axils of the adjacent lights are coupled to each other through flexible couplings allowing the positioning of one or more lights to dictate the position of all of the lights in each substantially circular tube.

In Example 16, the subject matter of Example 15 includes, wherein the flexible couplings include but are not limited to: cables, ball-shaped Allen wrench heads and sockets, "U joints" or "lock and key" connectors of various shapes.

In Example 17, the subject matter of Examples 10-16 includes, wherein the width of the substantially tubular light housings is less than three times the diameter of the LED reflectors.

Example 18 is an aerodynamic surgical light, the aerodynamic surgical light comprising: a light head made of one or more substantially tubular light housings; and the substantially tubular light housings contain and protect a plurality of LED lights and their respective reflectors that aim a light beam toward the lower side of the substantially tubular light housings; and the substantially tubular light housings are vertically elongate with a vertical dimension at least 1.5 times the horizontal width; and the vertically elongated substantially tubular light housings include upper sections that are aerodynamically curved or pointed to streamline airflow past the light housings; and the aerodynamic curves include but are not limited to: substantially parabolic shapes, substantially pointed shapes, substantially semicircular shapes and combinations thereof; and the upper sections of the substantially tubular light housings are made of molded plastic resin reinforced with carbon fibers or glass fibers; and the lower sections of the substantially tubular light housings are made of a clear moldable plastic; and the one or more substantially tubular light housings are formed into one or more concentric substantially circular tubes with open spaces between the one or more concentric substantially circular tubes; and wherein the one or more concentric substantially circular tubes with open spaces between the one or more concentric substantially circular tubes are connected together by spokes forming a "wheel and spoke" structure.

In Example 19, the subject matter of Example 18 includes, wherein the open spaces comprise greater than 40% of the projected surface area of the surgical light.

In Example 20, the subject matter of Examples 18-19 includes, wherein the plurality of LED lights and their respective reflectors in the one or more concentric substantially circular tubes are each mounted on axils that allow the reflector and light to pivot from a first position shining straight downward collectively creating a cylinder of light to a second position shining inward collectively creating a cone of light.

The aerodynamic surgical light of Example 20, wherein the adjacent axils of the adjacent lights are coupled to each other through flexible couplings allowing the positioning of one or more lights to dictate the position of all of the lights in each substantially circular tube.

In Example 21 the subject matter of example includes, wherein the flexible couplings include but are not limited to: cables, ball-shaped Allen wrench heads and sockets, "U joints" or "lock and key" connectors of various shapes.

In Example 22, the subject matter of Examples 18-21 includes, wherein the one or more substantially tubular light housings are connected together to form a geographic center of mass where the substantially tubular light housings connect to a ball and socket joint that connects the light housings to a supporting boom system.

In Example 23, the subject matter of Example 22 includes, wherein ball and socket and a light handle are connected at the center of the wheel and spoke structure.

Example 24 is an aerodynamic surgical light, the aerodynamic surgical light comprising: a light head made of one or more substantially tubular light housings; and the substantially tubular light housings contain and protect a plurality of LED lights and their respective reflectors that aim a light beam toward the lower side of the substantially tubular light housings; and the width of the substantially tubular light housings is less than three times the diameter of the LED reflectors; and the substantially tubular light housings are vertically elongate with a vertical dimension at least 1.5 times the horizontal width; and the vertically elongated substantially tubular light housings include upper sections that are aerodynamically curved or pointed to streamline airflow past the light housings; and the aerodynamic curves include but are not limited to: substantially parabolic shapes, substantially pointed shapes, substantially semicircular shapes and combinations thereof; and the upper sections of the substantially tubular light housings are made of molded plastic resin reinforced with carbon fibers or glass fibers; and the lower sections of the substantially tubular light housings are made of a clear moldable plastic; and the one or more substantially tubular light housings are formed into one or more concentric substantially circular tubes with open spaces between the one or more concentric substantially circular tubes; and the plurality of LED lights and their respective reflectors in the one or more concentric substantially circular tubes are each mounted on axils that allow the reflector and light to pivot from a first position shining straight downward collectively creating a cylinder of light to a second position shining inward collectively creating a cone of light; and wherein the adjacent axils of the adjacent lights are coupled to each other through flexible couplings allowing the positioning of one or more lights to dictate the position of all of the lights in each substantially circular tube.

In Example 25, wherein the open spaces comprise greater than 40% of the projected surface area of the surgical light.

In Example 26, the subject matter of Examples 24-25 includes, wherein the one or more concentric substantially circular tubes with open spaces between the one or more concentric substantially circular tubes are connected together by spokes forming a "wheel and spoke" structure.

In Example 27, the subject matter of Examples 24-26 includes, wherein the flexible couplings include but are not limited to: cables, ball-shaped Allen wrench heads and sockets, "U joints" or "lock and key" connectors of various shapes.

In Example 28, the subject matter of Examples 24-27 includes, wherein the one or more substantially tubular light housings are connected together to form a geographic center of mass where the substantially tubular light housings connect to a ball and socket joint that connects the light housings to a supporting boom system.

In Example 29, the subject matter of Examples 24-28 includes, wherein the width of the substantially tubular light housings is less than three times the diameter of the LED reflectors.

Example 30 is at least one machine-readable medium including instructions that, when executed by processing circuitry, cause the processing circuitry to perform operations to implement of any of Examples 1-29.

Example 31 is an apparatus comprising means to implement of any of Examples 1-29.

Example 32 is a system to implement of any of Examples 1-29.

Example 33 is a method to implement of any of Examples 1-29.

What is claimed is:

1. An aerodynamic surgical light comprising:
    a light head made of one or more substantially conical light housings;
    the one or more substantially conical light housings contain a plurality of LED lights and respective reflectors that aim a light beam toward a lower side of the one or more substantially conical light housings;
    the one or more substantially conical light housings are vertically elongate with a vertical dimension at least 1.2 times greater than a horizontal width;
    the one or more substantially conical light housings include upper sections that are aerodynamically curved or pointed to streamline airflow past the one or more substantially conical light housings;
    the aerodynamic curves include at least one of a substantially parabolic shape, a substantially pointed shape, a substantially semicircular shape, and combinations thereof; and
    the one or more substantially conical light housings are connected together to form a geographic center of mass where the one or more substantially conical light housings connect to a supporting boom system.

2. The aerodynamic surgical light of claim 1, wherein the one or more substantially conical light housings are formed into one or more concentric substantially circular tubes with open spaces between the one or more concentric substantially circular tubes.

3. The aerodynamic surgical light of claim 2, wherein the open spaces comprise greater than 30% of the projected surface area of the surgical light.

4. The aerodynamic surgical light of claim 2, wherein the one or more concentric substantially circular tubes with open spaces between the one or more concentric substantially circular tubes are connected together by spokes forming a wheel and spoke structure.

5. The aerodynamic surgical light of claim 4, wherein a ball and socket joint and a light handle are connected to the center of the wheel and spoke structure.

6. The aerodynamic surgical light of claim 1, wherein the plurality of LED lights and their respective reflectors in the one or more concentric substantially circular tubes are each mounted on axils that allow the reflector and light to pivot from a first position shining straight downward collectively creating a cylinder of light to a second position shining inward collectively creating a cone of light.

7. The aerodynamic surgical light of claim 6, wherein the adjacent axils of the adjacent lights are coupled to each other through flexible couplings allowing the positioning of one or more lights to dictate the position of all of the lights in each substantially circular tube.

8. The aerodynamic surgical light of claim 7, wherein the flexible couplings include ball-shaped Allen wrench heads and sockets connectors.

9. The aerodynamic surgical light of claim 1, wherein the upper sections of the one or more substantially conical light housings are made of plastic resin reinforced with carbon fibers or glass fibers and the lower sections of the one or more substantially conical light housings are made of a clear plastic.

10. An aerodynamic surgical light comprising:
    a light head made of one or more substantially conical light housings;
    the one or more substantially conical light housings contain a plurality of LED lights and respective reflectors that aim a light beam toward a lower side of the one or more substantially conical light housings;
    the one or more substantially conical light housings are vertically elongate with a vertical dimension at least 1.2 times greater than the horizontal width;
    the one or more substantially conical light housings include upper sections that are aerodynamically curved or pointed to streamline airflow past the light housings;
    the aerodynamic curves include at least one of substantially parabolic shapes, substantially pointed shapes, substantially semicircular shapes, and combinations thereof; and
    the one or more substantially conical light housings are formed into one or more concentric substantially circular tubes with open spaces between the one or more concentric substantially circular tubes,
    wherein the open spaces comprise greater than 30% of the projected surface area of the surgical light.

11. The aerodynamic surgical light of claim 10, wherein the one or more concentric substantially circular tubes with open spaces between the one or more concentric substantially circular tubes are connected together by spokes forming a wheel and spoke structure.

12. The aerodynamic surgical light of claim 11, wherein the one or more substantially conical light housings are connected together to form a geographic center of mass where the substantially conical light housings connect to a supporting boom system.

13. The aerodynamic surgical light of claim 12, wherein a ball and socket joint and a light handle are connected to the center of the wheel and spoke structure.

14. The aerodynamic surgical light of claim 10, wherein the plurality of LED lights and their respective reflectors in the one or more concentric substantially circular tubes are each mounted on axils that allow the reflector and light to pivot from a first position shining straight downward collectively creating a cylinder of light to a second position shining inward collectively creating a cone of light.

15. The aerodynamic surgical light of claim 14, wherein the adjacent axils of the adjacent lights are coupled to each other through flexible couplings allowing the positioning of one or more lights to dictate the position of all of the lights in each substantially circular tube.

16. The aerodynamic surgical light of claim 15, wherein the flexible couplings include ball-shaped Allen wrench heads and sockets connectors.

17. The aerodynamic surgical light of claim 10, wherein the upper sections of the one or more substantially conical light housings are made of plastic resin reinforced with carbon fibers or glass fibers and the lower sections of the one or more substantially conical light housings are made of a clear plastic.

18. An aerodynamic surgical light comprising:
   a light head made of one or more substantially conical light housings;
   the one or more substantially conical light housings contain and protect a plurality of LED lights and respective reflectors that aim a light beam toward the lower side of the substantially conical light housings;
   the substantially conical light housings are vertically elongate with a vertical dimension at least 1.2 times the horizontal width;
   the one or more substantially conical light housings include upper sections that are aerodynamically curved or pointed to streamline airflow past the light housings;
   the aerodynamic curves include at least one of substantially parabolic shapes, substantially pointed shapes, substantially semicircular shapes, and combinations thereof; and
   the one or more substantially conical light housings are formed into one or more concentric substantially circular tubes with open spaces between the one or more concentric substantially circular tubes,
   wherein the one or more concentric substantially circular tubes with open spaces between the one or more concentric substantially circular tubes are connected together by spokes forming a wheel and spoke structure.

19. The aerodynamic surgical light of claim 18, wherein the open spaces comprise greater than 30% of the projected surface area of the surgical light.

20. The aerodynamic surgical light of claim 18, wherein the plurality of LED lights and their respective reflectors in the one or more concentric substantially circular tubes are each mounted on axils that allow the reflector and light to pivot from a first position shining straight downward collectively creating a cylinder of light to a second position shining inward collectively creating a cone of light.

21. The aerodynamic surgical light of claim 20, wherein the adjacent axils of the adjacent lights are coupled to each other through flexible couplings allowing the positioning of one or more lights to dictate the position of all of the lights in each substantially circular tube.

22. The aerodynamic surgical light of claim 18, wherein the upper sections of the one or more substantially conical light housings are made of plastic resin reinforced with carbon fibers or glass fibers and the lower sections of the one or more substantially conical light housings are made of a clear plastic.

23. The aerodynamic surgical light of claim 18, wherein the one or more substantially conical light housings are connected together to form a geographic center of mass where the substantially conical light housings connect to a supporting boom system.

24. The aerodynamic surgical light of claim 23, wherein a ball and socket joint and a light handle are connected at the center of the wheel and spoke structure.

25. An aerodynamic surgical light comprising:
   a light head made of one or more substantially conical light housings;
   the one or more substantially conical light housings contain a plurality of LED lights and respective reflectors that aim a light beam toward the lower side of the substantially conical light housings;
   the one or more substantially conical light housings are vertically elongate with a vertical dimension at least 1.2 times the horizontal width;
   the one or more substantially conical light housings include upper sections that are aerodynamically curved or pointed to streamline airflow past the light housings;
   the aerodynamic curves include at least one of substantially parabolic shapes, substantially pointed shapes, substantially semicircular shapes, and combinations thereof;
   the one or more substantially conical light housings are formed into one or more concentric substantially circular tubes with open spaces between the one or more concentric substantially circular tubes; and
   the plurality of LED lights and respective reflectors in the one or more concentric substantially circular tubes are each mounted on axils that allow the reflector and light to pivot from a first position shining straight downward collectively creating a cylinder of light to a second position shining inward collectively creating a cone of light,
   wherein the adjacent axils of the adjacent lights are coupled to each other through flexible couplings allowing the positioning of one or more lights to dictate the position of all of the lights in each substantially circular tube.

26. The aerodynamic surgical light of claim 25, wherein the open spaces comprise greater than 30% of the projected surface area of the surgical light.

27. The aerodynamic surgical light of claim 25, wherein the one or more concentric substantially circular tubes with open spaces between the one or more concentric substantially circular tubes are connected together by spokes forming a wheel and spoke structure.

28. The aerodynamic surgical light of claim 25, wherein the upper sections of the one or more substantially conical light housings are made of plastic resin reinforced with carbon fibers or glass fibers and the lower sections of the one or more substantially conical light housings are made of a clear plastic.

29. The aerodynamic surgical light of claim 25, wherein the one or more substantially conical light housings are connected together to form a geographic center of mass where the substantially conical light housings connect to a supporting boom system.

30. The aerodynamic surgical tight of claim 25, wherein the width of the substantially conical light housings is less than three times the diameter of the LED reflectors.

* * * * *

UNITED STATES PATENT AND TRADEMARK OFFICE
CERTIFICATE OF CORRECTION

| | |
|---|---|
| PATENT NO. | : 11,602,410 B1 |
| APPLICATION NO. | : 17/987125 |
| DATED | : March 14, 2023 |
| INVENTOR(S) | : Scott D. Augustine |

It is certified that error appears in the above-identified patent and that said Letters Patent is hereby corrected as shown below:

In the Claims

In Column 21, Line 4, in Claim 30, delete "tight" and insert --light-- therefor

Signed and Sealed this
Twenty-fifth Day of April, 2023

*Katherine Kelly Vidal*

Katherine Kelly Vidal
*Director of the United States Patent and Trademark Office*